(12) United States Patent
Ringermacher et al.

(10) Patent No.: US 6,394,646 B1
(45) Date of Patent: May 28, 2002

(54) METHOD AND APPARATUS FOR QUANTITATIVE NONDESTRUCTIVE EVALUATION OF METAL AIRFOILS USING HIGH RESOLUTION TRANSIENT THERMOGRAPHY

(75) Inventors: Harry Israel Ringermacher, Delanson; Donald Robert Howard, Troy; Ravindra Kumar Pandey, Albany, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/292,886

(22) Filed: Apr. 16, 1999

(51) Int. Cl.$^7$ .............................................. G01N 25/72
(52) U.S. Cl. ........................ 374/7; 374/5; 250/341.6; 250/330
(58) Field of Search ........................... 374/4, 5, 6, 7, 374/124; 250/341.6, 330, 332

(56) References Cited

U.S. PATENT DOCUMENTS

| | | | |
|---|---|---|---|
| 3,808,439 A | * | 4/1974 | Renius ........................ 374/4 |
| 4,513,384 A | | 4/1985 | Rosencwaig .................. 374/4 |
| 4,768,158 A | | 8/1988 | Osanai | |

(List continued on next page.)

FOREIGN PATENT DOCUMENTS

| | | | |
|---|---|---|---|
| EP | 0304708 | 3/1989 | |
| EP | 586901 A1 | * 3/1994 | .................. 374/4 |
| GB | 2 168 494 | 6/1986 | |
| GB | 2 220 065 | 12/1989 | |
| JP | 0057135 | 3/1989 | ................ 374/137 |
| JP | 02264832 A | * 1/1990 | ................ 374/121 |
| JP | 04050734 A | * 2/1992 | ................ 374/121 |
| JP | 10274675 | 10/1998 | |
| WO | 9805921 | 2/1998 | |
| WO | 98/05949 | 2/1998 | |

OTHER PUBLICATIONS

Lotti, et al., "Flow recognition in composites by processing sequences infrared images," vol. 2, Proc. 3rd Intl Workshop, Cappellini, V., ED, 1990, pp. 232–240.

Buchanan, R. A., et al., "Recent Advances in digital thermography for nondestructive evaluation", SPIE vol. 1313 Thermosense XII (1990), pp. 134–ff.

(List continued on next page.)

Primary Examiner—Diego Gutierrez
Assistant Examiner—Stanley J. Pruchnic, Jr.
(74) Attorney, Agent, or Firm—Penny Clarke; Donald S. Ingraham (57) ABSTRACT

An IR transient thermography imaging system includes high-power flash lamps fitted with spectrally tuned optical filters and a focal-plane array camera for IR image data acquisition. The image data processing control computer analyzes acquired IR image data frames and provides a color-keyed display of an imaged object that correlates to object thickness over the imaged surface area. Acquisition of IR data is initiated at a firing of flash lamps used to heat a surface of the object along with a reference standard. A predetermined number of IR image frames are acquired and recorded over a predetermined period of time after firing of the lamps to develop a temperature-time (T-t) history of the object surface and the reference standard. A contrast curve is calculated for each pixel in the image frame, each pixel corresponding to an elemental region on the object surface. Gaussian temporal smoothing of contrast curve data is performed to improve signal-to-noise characteristics and a derivative of the contrast curve is determined using data points mathematically related to image frame number. All local peaks in the derivative of the contrast curve are identified and given significance according to a predetermined weighting function. The frame number of the most significant peak is used to determine time of occurrence of an "inflection point" in the contrast curve which is then used in determining object thickness. Gain correction of pixel intensity data is employed to offset IR emissivity variations caused by surface curvatures and varying surface conditions on an object.

22 Claims, 2 Drawing Sheets

U.S. PATENT DOCUMENTS

| | | | |
|---|---|---|---|
| 4,792,683 | A | 12/1988 | Chang et al. |
| 4,854,724 | A | 8/1989 | Adams et al. |
| 5,032,727 | A | 7/1991 | Cox, Jr. et al. |
| 5,246,291 | A | 9/1993 | Lebeau et al. |
| 5,250,809 | A | 10/1993 | Nakata et al. |
| 5,292,195 | A | 3/1994 | Crisman, Jr. |
| 5,539,656 | A | 7/1996 | Annigeri et al. |
| 5,582,485 | A | 12/1996 | Lesniak |
| 5,631,465 | A | 5/1997 | Shepard |
| 5,683,181 | A | 11/1997 | Shepard |
| 5,711,603 | A | 1/1998 | Ringermacher et al. |

OTHER PUBLICATIONS

Speedotron® Instruction Manual for Speedotron Brown Line Equipment, Speedotron Corp., 32 Pages, 1997.*

Becker et al., Method of Determining The Wall Thickness of a Turbine Blade and Device for Carrying out This Method, English Translation (PTO 01–927) of WO 98/05921 A1, Feb. 1998.*

Ballard et. al., "Computer–Based Thermographic Displays and Real–Time Techniques," in IEEE Transactions on Industrial Electronics and Control Instr, vol. IECI–20, No. 4, Nov. 1973, pp. 200–205.*

Milne, J. M., et al., "The non–destructive evaluation of composites and other materials by thermal pulse video thermography", SPIE vol. 520 Thermosense VII (1984), 4 pages.*

Milne, J. M., et al., "Application of thermal pulses and infrared thermal imagers for observing sub–surface structures in metals and composites", SPIE vol. 590 (1985), pp. 293–298.*

Article entitled "Thermal NDE System", Aerospace Engineering, Oct. 1995, p. 7.

Article entitled "Thermal Evaluation Reveals Depth Detail", Photonics Spectra, Jun. 1995, pp. 21–22.

Ringermacher, H.I. et al., "Towards a Flat–Bottom Hole Standard for Thermal Imaging", Review of Progress in Quantitative Nondestructive Evaluation, vol. 17A, Edited by D.O. Thompson and D.E. Chimenti, Plenum Press, New York, May 1998, pp. 425–429.

* cited by examiner fig. 1 fig. 2

METHOD AND APPARATUS FOR QUANTITATIVE NONDESTRUCTIVE EVALUATION OF METAL AIRFOILS USING HIGH RESOLUTION TRANSIENT THERMOGRAPHY

TECHNICAL FIELD

The present invention relates to thermographic nondestructive testing techniques for determining the thickness of an object. More particularly, the present invention relates to a high speed infrared transient thermography method and apparatus for accurately measuring the wall thickness of metal turbine rotor blades or the like.

BACKGROUND

Over the years, various nondestructive ultrasonic measurement techniques have been utilized to determine cross-sectional thickness of cast metal and other solid objects. Conventionally, the object is probed with ultrasonic waves which penetrate the surface and are reflected internally at the opposite side or surface of the object. Based upon the time required to receive a reflected wave, the distance to the opposite (back) side can be determined—giving the thickness of the object at that point. Unfortunately, conducting ultrasonic measurements of this sort to examine the cross-sectional thickness for most of an object would usually necessitate a cumbersome and time-consuming mechanical scanning of the entire surface with a transducer. In addition, to facilitate intimate sonic contact between the transducer and the object surface, a stream of liquid couplant must be applied to the surface or, alternatively, total immersion of the object in the couplant must be accommodated. Such accommodations, however, are most often not very practical or even feasible for numerous structural and material reasons. For example, ultrasonic systems capable of scanning and analyzing geometrically complex parts are typically very expensive and complicated. In addition, a mechanical scanning of the transducer over the surface of a large object can literally take hours.

Moreover, when conducting ultrasonic measurements on certain metal objects, the internal crystal orientation and structure of the metal can cause undesirable noise and directional effects that contribute to inaccuracies in the acquired data. This inherent limitation of ultrasonic measurements proves to be a serious drawback when testing components constructed of crystalline or "directional" metals such as often used in contemporary turbine airfoils.

In contrast, infrared (IR) transient thermography is a somewhat more versatile nondestructive testing technique that relies upon temporal measurements of heat transference through an object to provide information concerning the structure and integrity of the object. Since heat flow through an object is substantially unaffected by the micro-structure and the single-crystal orientations of the material of the object, an infrared transient thermography analysis is essentially free of the limitations this creates for ultrasonic measurements. In contrast to most ultrasonic techniques, a transient thermographic analysis approach is not significantly hampered by the size, contour or shape of the object being tested and, moreover, can be accomplished ten to one-hundred times faster than most conventional ultrasonic methods if testing objects of large surface area.

One known contemporary application of transient thermography, which provides the ability to determine the size and "relative" location (depth) of flaws within solid non-metal composites, is revealed in U.S. Pat. No. 5,711,603 to Ringermacher et al., entitled "Nondestructive Testing: Transient Depth Thermography"; and is incorporated herein by reference. Basically, this technique involves heating the surface of an object of interest and recording the temperature changes over time of very small regions or "resolution elements" on the surface of the object. These surface temperature changes are related to characteristic dynamics of heat flow through the object, which is affected by the presence of flaws. Accordingly, the size and a value indicative of a "relative" depth of a flaw (i.e., relative to other flaws within the object) can be determined based upon a careful analysis of the temperature changes occurring at each resolution element over the surface of the object. Although not explicitly disclosed in the above referenced Ringermacher patent, the "actual" depth of a flaw (i.e., the depth of a flaw from the surface of the object) can not be determined unless a "standards block", having voids at known depths, or an "infinite" (thermally thick) reference region on the object is included as part of the thermographic data acquisition and analysis for comparison against the relative depth values.

To obtain accurate thermal measurements using transient thermography, the surface of an object must be heated to a particular temperature in a sufficiently short period of time so as to preclude any significant heating of the remainder of the object. Depending on the thickness and material characteristics of the object under test, a quartz lamp or a high intensity flash-lamp is conventionally used to generate a heat pulse of the proper magnitude and duration. However, the specific mechanism used to heat the object surface could be any means capable of quickly heating the surface to a temperature sufficient to permit thermographic monitoring—such as, for example, pulsed laser light). Once the surface of the object is heated, a graphic record of thermal changes over the surface is acquired and analyzed.

Conventionally, an infrared (IR) video camera has been used to record and store successive thermal images (frames) of an object surface after heating it. Each video image is composed of a fixed number of pixels. In this context, a pixel is a small picture element in an image array or frame which corresponds to a rectangular area, called a "resolution element", on the surface of the object being imaged. Since, the temperature at each resolution element is directly related to the intensity of the corresponding pixel, temperature changes at each resolution element on the object surface can be analyzed in terms of changes in pixel contrast. The stored video images are used to determine the contrast of each pixel in an image frame by subtracting the mean pixel intensity for a particular image frame, representing a known point in time, from the individual pixel intensity at that same point in time.

The contrast data for each pixel is then analyzed in the time domain (i.e., over many image frames) to identify the time of occurrence of an "inflection point" of the contrast curve data, which is mathematically related to a relative depth of a flaw within the object. Basically, as applied to an exemplary "plate" like object of consistent material and thickness L, a heat flux pulse impinging on an object takes a certain "characteristic time", $T_c$, to penetrate through the object to the opposite side (back wall) and return to the front surface being imaged. This characteristic time, $T_c$, is related to the thickness of the object, given the thermal diffusivity of the material by the following equation:

$$T_c = 4L^2/\pi^2 \alpha \qquad \text{Equ. (1)}$$

where L is the thickness (cm) of the object and $\alpha$ is the thermal diffusivity ($cm^2$/sec) of the material.

From empirical observations it is known that after a heat pulse impinges on a plate-like object, the surface temperature observed from the same side of the object (i.e., the front) rises in a fashion that is also dependent on the thickness and the thermal diffusivity of the material. Moreover, from a graph of the time vs. temperature (T-t) history of the surface, one can determine the characteristic time, $T_c$, in terms of a unique point on the T-t curve, called the "inflection point." This inflection point, $t_{infl}$, is indicated by the point of maximum slope on the T-t curve (i.e., peak-slope time) and is related to the characteristic time, $T_c$, by the following equation:

$$t_{infl} = 0.9055\, T_c \qquad \text{Equ. (2)}$$

This relationship between the inflection point and the characteristic time, as expressed by Equ. (2) above, is precise to approximately 1% for one-dimensional (1-D), as well as two-dimensional (2-D), heat flow analysis. Once an inflection point, $t_{infl}$, is determined from the T-t response, a relative thickness, L, of the object can be determined from Equ. (1) using the known thermal diffusivity, $\alpha$, of the material and the actual value of $T_c$ from Equ (2).

In this regard, a more detailed discussion of the heat-flow invariant relationship between the peak-slope time (inflection point) and the material "characteristic time" as defined above may be found in the *Review Of Progress In Quantitative Nondestructive Evaluation*, in an article by Ringermacher et al., entitled "Towards A Flat-Bottom Hole Standard For Thermal Imaging", published May 1998 by Plenum Press, New York, which is incorporated herein by reference.

Unfortunately, although the above referenced Ringermacher et al. patented method for flaw detection may be effective on ceramics, plastics, composites and other non-metallic objects, it is not particularly feasible for use in determining the thickness of metal objects. One of the problems is that metals have significantly higher thermal conductivity and thermal diffusion characteristics than non-metals. This decreases the time period during which useful thermal data can be acquired and requires increasing the sensitivity of the IR recording equipment. The increased sensitivity of the equipment causes inaccuracies in the acquired data arising from IR noise from other ambient IR sources such as the flash-lamps. Moreover, since the apparatus and method of the above referenced Ringermacher et al. patent only produces "relative" measurements, it can not be used to obtain a value for the actual thickness of a metal object at a desired point. Consequently, an improved method of conducting and processing IR transient thermography for determining the actual thickness of metal objects is needed.

DISCLOSURE OF THE INVENTION

The present invention relates to a nondestructive testing method and apparatus for determining and displaying the actual thickness of an object through the use of high speed infrared (IR) transient thermography. A unique aspect of the present invention is that the object of interest can be a metal material, even though metals have high rates of thermal conduction.

In accordance with the present invention, an improved high speed IR transient thermography arrangement—based upon known heat flow dynamics within metal objects—is utilized to accurately measure the thickness of a metal object and provide a visual color-coded display indicative of its cross-sectional thickness over a desired area of the object. Moreover, the improved transient thermographic techniques of the present invention can be used to measure the thickness of metal objects with greater accuracy than conventional ultrasonic methods.

In this regard, the present invention makes particular use of the inflection point in the analysis of metal objects because the inflection point occurs relatively early in the T-t response and is essentially independent of lateral heat loss mechanisms. Such considerations are important when working with metal objects since, due to the high thermal conductivity of metals, the thermal response is fast and, thus, the available observation time will be short. Moreover, in accordance with the present invention, when a T-t curve is obtained from "front-side" IR camera observations, a more accurate determination of the inflection point is obtained if an image "contrast" curve is created by subtracting the observed T-t curve from a hypothetical or measured T-t curve reflecting a deep interior "reference region" within the heated object (this reference region approximating an "infinitely thick" object) or in an adjacent thermally thick "reference" block.

With the present invention, the inflection point, $t_{infl}$, is determined from thermal data obtained over a predetermined time period from successive IR camera image frames. This time period is preferably at least somewhat longer than an anticipated characteristic time, as obtained from Equ. (1), based on an estimation of the thickness of the object being evaluated.

Unfortunately, as recognized by the inventors of the present invention, the known prior art IR transient thermography apparatus has at least one drawback: the flash-lamps required for generating the heating pulse produce long-wave IR "afterglow" emissions that ultimately reach the object and the camera as background radiation. This results in a reduced contrast within the recorded IR images and ultimately affects the accuracy of the thermal measurements. Accordingly, the present invention provides an improved high speed IR transient thermography apparatus that substantially eliminates problems associated with "afterglow" IR emissions caused by conventional flash-lamp heating arrangements. In addition, the present invention provides an improved IR transient thermographic method and apparatus for effective quantitative evaluation of the front wall thickness of metal objects such as turbine rotor blades or the like. Furthermore, the present invention provides an improved method and apparatus for determining the thickness of a metal object, wherein the means for acquiring data for determining the thickness is substantially unaffected by the particular internal crystalline structure of the object, such as are common to metal castings and other "directional" metal objects.

In accordance with a preferred embodiment of the present invention, the apparatus includes an imaging system comprising one or more high power flash lamps fitted with special optical filters, an IR sensitive focal-plane array camera for data acquisition and a display monitor. A computer system controls the imaging system, records and analyzes surface temperature data acquired via the IR camera and provides a color-keyed image on the display monitor that accurately corresponds to thickness of the object.

The acquisition of surface temperature data is initiated by firing the flash-lamps to illuminate the surface of the object. The special optical filters are spectrally tuned to absorb and/or reflect all 3–5 micron IR radiation back into the flash-lamp(s). This prevents undesirable long-wave IR "afterglow" emissions—typically generated by overheated metallic elements in the flash-lamps after the lamps are extinguished—from reaching the object or the camera. The use of such filters enables a more precise thermal evaluation that can produce dimensional measurements within an accuracy range of 1%–3% of actual thickness.

A predetermined number of image frames are then recorded over a period of time after the flash lamps are fired and the recorded images used to develop a temperature-time (T-t) history for every elemental region or "resolution element" over the region of interest on the object surface. Each recorded image frame is comprised of a predetermined (n×m) array of image pixels whose intensity correlate to the surface temperature of the object at the time the frame data was acquired—each pixel having an (x,y) location designation within the image frame that corresponds to a particular resolution element.

A heat flow analysis of the T-t history is then conducted for each pixel in the acquired image frames to determine the thickness of the object at each resolution element location (either a one-dimensional or a multi-dimensional heat flow analysis approach may be used). Conventionally, analysis of transient heat flow through solid portions of an object requires determining the characteristic time, $T_c$, required for a "pulse" of thermal energy to penetrate the object at a first surface, reflect off an opposite surface and return to the first surface. Since the characteristic time is related to the distance between the two surfaces, it can be used to determine the thickness of the object between the two surfaces at a desired point. Fortunately, a value for characteristic time $T_c$ may be determined from the thermographic T-t history of a pixel since it is related in time to the occurrence of an "inflection point" in the recorded contrast history of the pixel according to Equ. (2) above.

An improved heat flow analysis method is also provided in accordance with the present invention that, among other things, facilitates a more accurate determination of the contrast history "inflection point." As described in greater detail below, a contrast curve is first determined for each (x,y) pixel location corresponding to each resolution element of the object surface. This contrast curve is formulated based on an average pixel intensity obtained using a "thermally thick" portion (in a preferred embodiment the thermally thick portion is at least five (5) times as thick as the total thickness of the object being measured) of the object or of a different "reference" block having thermal conductivity similar to the object being measured. In a preferred embodiment, a separate thermally thick block is positioned adjacent the object being measured and imaged together with it. In another embodiment, a "standards" block having a thermally thick portion and comprising different steps of known thickness is thermographically imaged together with the object of interest.

Next, Gaussian temporal smoothing of the pixel contrast curve data is employed to improve the signal-to-noise ratio of the measurements. The mathematical derivative of the contrast curve is then calculated using three-point data sampling having a first and third sample point separation that is proportionally related to the value of the image frame number at the second sample point. Next, local peaks in the derivative of the contrast curve data are determined and a weighting function is used to adjust the significance of each peak to identify a best "inflection point" in the T-t contrast curve data for use in determining object thickness. Correction of image pixel data is also employed to offset the effects of varying IR emissivity due to surface curvatures of the imaged object.

BRIEF DESCRIPTION OF THE DRAWINGS

The purpose and advantages gained by the present invention will be understood by careful study of the following detailed description of the presently preferred embodiment with particular reference to the accompanying drawings.

BEST MODE FOR CARRYING OUT THE INVENTION

Figure 1:
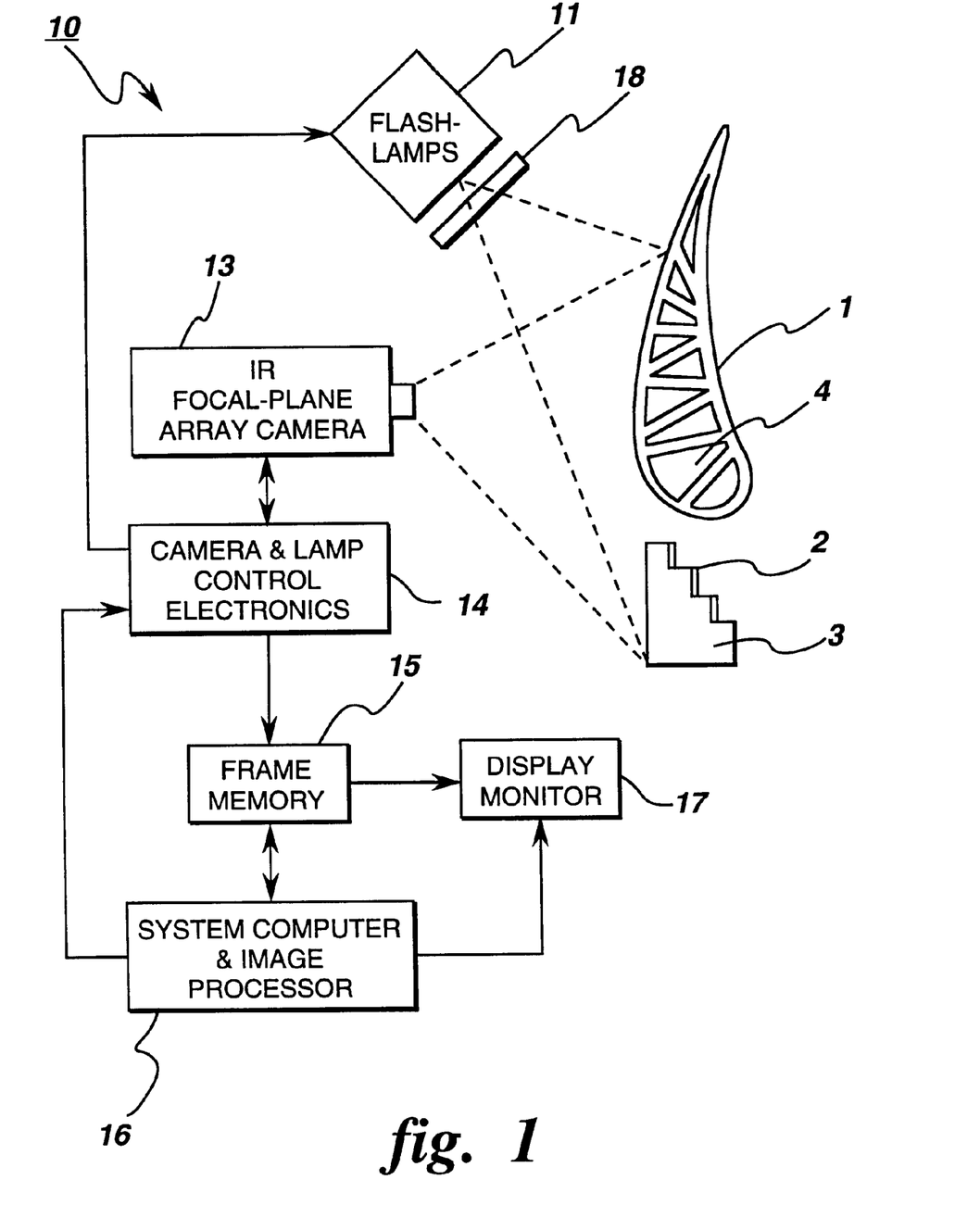
FIG. 1 is schematic diagram illustrating an example infrared transient thermography system arrangement for determining and displaying the actual thickness of an object in accordance with the present invention.

FIG. 1 illustrates an example IR transient thermography system 10 for determining and displaying the thickness of an object, e.g., a metal turbine airfoil 1 having intentional voids 4. For the purposes of the following discussion, the "thickness" of an object refers to a front wall or surface thickness in the context of a hollow or semi-hollow object (i.e., an object having an intentional void) and a "thermally thick" object refers to an object or portion of an object that is thick enough to approximate a hypothetical "infinitely" thick object (which in a preferred embodiment is at least five (5) times as thick as the total thickness of the object being measured).

Preferably, the object being measured is first painted (e.g., by spray, brush or roller) with a thin quick-drying coating of a high-ultraviolet, visible light, and infrared-absorbency substance—for example, a carbon based material such as graphite, carbon, or carbon-black water-based paint.

In the present invention, a flash-lamp heat-pulse source 11 is triggered to rapidly heat the surface of the object being measured. One suitable arrangement for flash-lamp heat-pulse source 11 would be, for example, a set of four or eight high-speed, high output power photographic flash-lamps, each capable of about 4.8 Kilo-joules output and having individual power supplies (such as manufactured by Speedotron, Corp. in Chicago, Ill.).

Since metals have a significantly faster rate of heat conduction than non-metals, the characteristic times for heat flow in metals are much faster than those of, for example, plastic or composite materials. Consequently, in attempting to adapt conventional IR thermography techniques (ordinarily limited to non-metals) to metals, a sharp cutoff in the applied heat is needed. In order to obtain this, a 3–5 micron reflective filter 18 is used between (covering) flash-lamps 11 and object of interest 1 so as to prevent exposing the object to residual heat as the flashlamps cool down after exposure.

In practice, one or more filters may be used (e.g., one per each flash-lamp). These filters act to prevent direct long wave radiation—typically generated from the "afterglow" of overheated metallic elements in the flash-lamps—from ever leaving the flash-lamps and impinging on the target or otherwise reflecting back into focal-plane array camera 13. Such primary afterglow radiation from flash-lamps 11 competes and can interfere with the long-wave IR emissions from the targeted object during early thermal data acquisition, thus obscuring the true target-generated IR radiation and reducing ultimate image contrast and quality. Thus, the use of these special filters produces a sufficiently sharp heat pulse to enable the shorter heat travel time in metal to be detected.

In accordance with the present invention, flash-lamp filter 18 may be composed of Pyrex™, fused quartz, BK7, or other optical material that is transparent to visible and UV light and is coated on the flash-lamp facing side with an infrared-reflective coating to reflect all radiation in the 3–5 micron range back into the flash-lamps. (Optical glass and coated filters may be acquired or specially manufactured by a general scientific optics and optical glass manufacturer such as Oriel in Strafford, Conn.).

Surface temperature measurements of heat-pulse illuminated object 1, along with reference block 2, are acquired using a infrared (IR) sensitive imaging system comprising an IR sensitive focal-plane array camera 13 (e.g., a Radiance HS camera available from Amber Engineering in Goleta, Calif.—a Raytheon Company), control electronics 14, frame data memory 15, control computer/image processor 16 and display monitor 17.

Acquisition of thermal data is preferably initiated at the time of flash lamp firing either by optical triggering or by other suitable means. Flash-lamp firing is controlled via conventional flash-lamp electronics 14 managed by conventional video frame acquisition software running on system computer 16 (such as provided by the ImageDesk™ frame acquisition system from Amber Corp. or other conventional frame acquisition and flash-lamp control software, for example, such as commercially available from Thermal Wave Imaging Inc. in Lathrup Village, Mich.).

The system control computer/image processor 16 is a specially programmed general purpose digital computer that is capable of peripheral equipment control and communication functions in addition to digital image processing and display in accordance with the method of the present invention. System computer 16 controls camera and lamp electronics 14 and frame data memory 15 to acquire a predetermined number of successive thermal image frames of the object surface which are stored in memory 15 for future analysis.

Before beginning the thermal imaging process, IR camera 13 is first calibrated using a "full-field" dual-image calibration technique as now described. This preferred technique employs two "black-body" (BB) image calibration references: a BB "cold" source using a room-temperature flat-black plate and a BB "hot" source using a heated flat-black plate. For example, for acquiring the BB "cold" source calibration image, a flat-black painted box enclosing the room-temperature flat-black plate, arranged at a 45° angle to the camera lens, is placed directly in front of the lens. For acquiring the BB "hot" source calibration image, the camera lens is placed into the same flat-black painted box unit after heating the flat-black plate—nominally to about 10° C. above ambient—such that the camera images the heated plate over its full field. Although the above described dual-image calibration technique is preferred, any calibration technique that results in producing maximum uniformity of the image field—which is important for high contrast imaging and obtaining improved thermal accuracy—can be used.

Each image frame acquired during the imaging process consists of N×N pixels—each pixel corresponding to a resolution element on the object surface—where N is typically either 128 or 256 depending on the resolution and accuracy desired. Each pixel occupies about two bytes of storage memory and may be represented, for example, by a 12-bit or larger binary number. The stored image frames are sequentially identified with increasing frame number values which together serve to provide a historical record of the temperature vs time (T-t) characteristics of a front surface of object 1 for a predetermined period after being struck by the heat impulse imparted by flash lamp 11.

In a preferred embodiment, to determine an actual thickness of a metal object, the metal object of interest is positioned adjacent a separate metal reference block, 2, of similar composition and having a thermally thick portion 3, and is imaged together with block 2 within the same image frame using the same flash-lamp heating pulse. Thermally thick portion 3 of metal reference block 2 is used to permit the derivation of an average pixel intensity for the block that is unaffected by any possible influence of the heat-pulse reflected internally in the object being measured. This average pixel intensity is then used for determining individual pixel contrast (as described below) and permits an accurate actual thickness determination for the metal layer "under" that pixel.

During evaluation of a metal object, after control computer 16 triggers the firing of flash-lamp(s) 11, image data frames are acquired from camera 13 and the IR intensity at each resolution element on the image is digitally recorded and stored in frame data recorder 15. Data acquisition continues over a predetermined number of sequential image frames that are sufficient to acquire a meaningful T-t history over a duration of at least one estimated "characteristic time" for the material of the object. The number, Z, of image frames acquired varies depending on the accuracy and image resolution desired and can be as high as 550 frames per second of data acquisition.

Frame data recorder 15 may be a conventional digital memory internal to processor 16 or any suitable video frame data storage device accessible by processor 16. Each successive thermal image frame acquired is assigned an increasing frame number, Z, corresponding to the passage of real time. The resulting data frame "stack" is then analyzed taking a one-dimensional heat flow analysis approach, as outlined above. In accordance with this approach, the method of the present invention takes advantage of a known thermal invariance property—evidenced in the temperature vs time (T-t) history of each image pixel over successive IR image frames—that relies on identifying the location of an "inflection point" or peak-slope time, i.e., the point in time of maximum slope on the T-t data curve.

Figure 2:
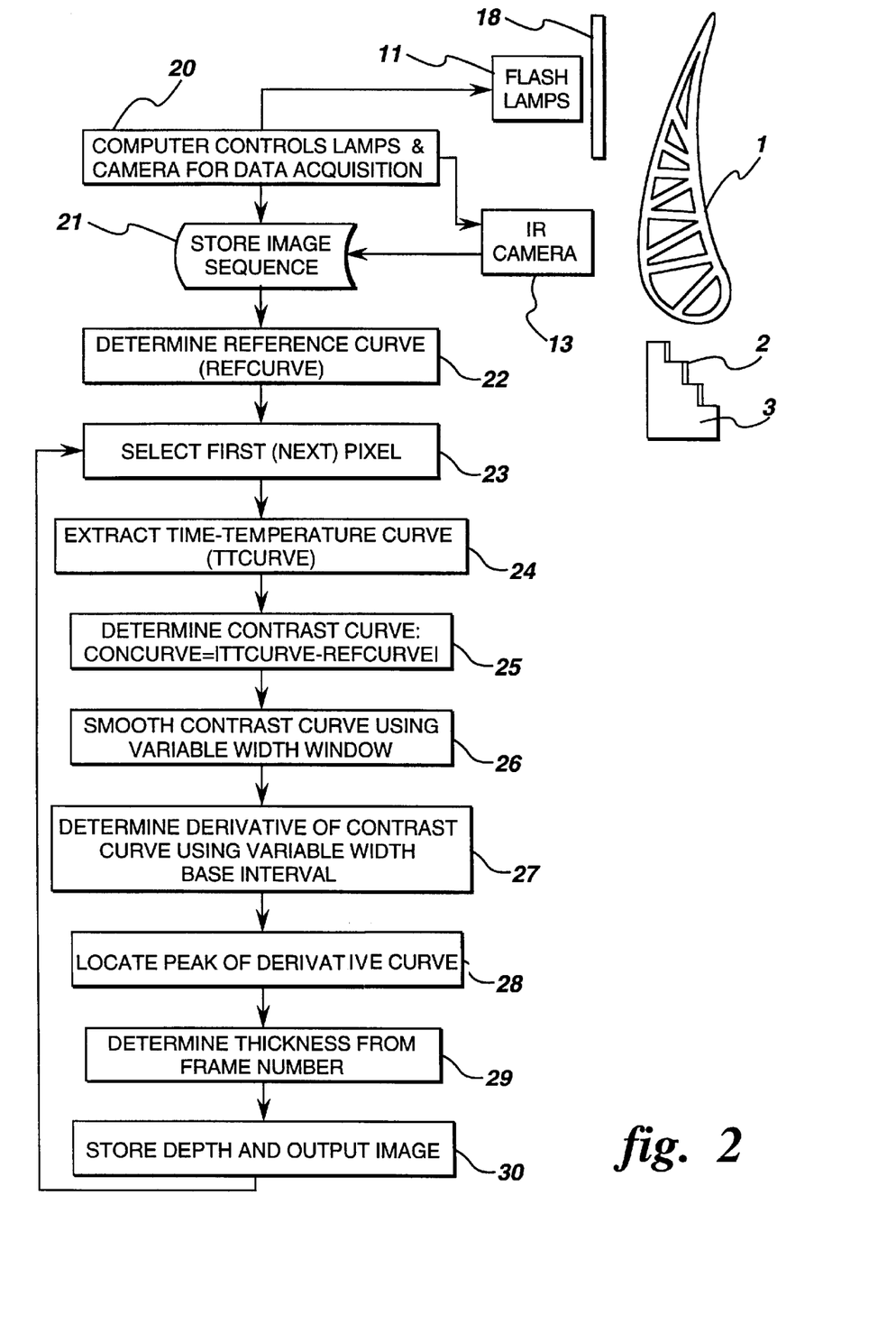
FIG. 2 is a flowchart illustrating the process of infrared image data acquisition and analysis as performed by the system of FIG. 1 in accordance with the present invention.

Referring now to FIG. 2, a flow diagram is presented that illustrates steps for conducting transient IR thermography and image data analysis for metal objects in accordance with the present invention. These steps are implemented by system computer 16 programmed using appropriate commercially available software and/or applying known conventional programming techniques.

First, a computer operator selects and/or inputs information concerning the relevant parameters for the desired material such as thermal diffusivity coefficient, the internal reference region thermal data, etc., and the region of interest on the object is identified (i.e., the IR camera is focused to capture the region of interest and a desired "thermally thick" region).

Next, with reference to step 20, the system control computer instructs the flash-lamp electronics to fire flash-lamps 11 and initiate image frame data acquisition from the focal plane array IR camera 13. Data acquisition proceeds over a predetermined number of sequential image frames. With reference to step 21, each sequentially acquired image frame is identified by a frame number of increasing value, Z, and then recorded in the frame data memory.

Next, with reference to step 22, a set of T-t curves is developed for each pixel in the thermal image corresponding to each (x,y) resolution element location over the region of interest on the surface of the object; the time and frame number of the initial IR heating "flash" is identified; a first unsaturated data frame is identified; and a "reference" T-t curve (refcurve) is generated. For determining the actual thickness at a resolution element location on the object (as opposed to a "relative thickness" which is merely a thickness value relative to other locations on the object), a reference T-t curve approximating the characteristics of a hypothetical "infinitely thick" object of similar heat conductivity characteristics must be used. To generate this reference curve, a thermally thick region of a separate article of similar composition is imaged along with the object and used to provide the reference T-t curve data. Alternately, T-t data from a known thermally thick portion of the object of interest can be used (or if only a relative thickness is desired, the reference curve data can be obtained from a T-t history of mean pixel intensity from each image frame).

Referring to steps 23 and 24, a first pixel (or a next pixel) is then selected for analysis and its T-t curve data (ttcurve) is extracted (i.e., determined or recalled from computer memory). At this point, optional offset and scale (amplitude) adjustments can be made to help overcome the effects of varying emissivity or loss of amplitude due to curvature on the object surface. To accomplish this, the T-t data curve for each pixel is adjusted to match specific points on a "normalized" reference curve. For example, the reference curve (refcurve) may be normalized so that the "cold" (pre-flash) amplitude corresponds to zero. As the T-t data curve for each pixel is then analyzed, it is offset to a cold amplitude of zero by first matching it to the appropriate point on the reference curve. In addition, a "gain" correction of the pixel intensity data can be applied to each pixel T-t data curve at this step to compensate for the effects of varying IR emissivity due to surface curvatures and/or variable surface conditions of the object; or for example, a pixel gain correction may be applied so that the pixel amplitude at the first unsaturated image frame will match the amplitude of the reference curve at the same point in time.

Next, with reference to step 25, in order to more accurately determine the inflection point in the T-t curve, a "contrast" curve (concurve) for the selected pixel is determined by subtracting the "reference" T-t curve data (refcurve) from the T-t curve (ttcurve) data of the pixel.

Next, with reference to step 26, a Gaussian function temporal smoothing of the contrast curve data is performed. Here, the "temporal window" used in the Gaussian smoothing algorithm is made to vary as a function of time by making it proportional to the image frame number, Z. Essentially, this smoothing "window" controls the full-width of the Gaussian at half-maximum (i.e., the "2-$\sigma$" width). Taking this variable width "frame-number smoothing" approach is more advantageous than using traditional Gaussian smoothing because it tends to compensate for the effects of heat diffusion at increasing depths within the material.

Preferably, for this step, the width of the smoothing window at a selected data point is made proportional to the square-root of the image frame number at that point. In addition to Gaussian temporal smoothing, a number of software implemented "imaging filters" may also be applied to the contrast curve data at this stage, including spatial smoothing, initial and ending noise suppression, negative contrast suppression and contrast thresholding.

Next, with reference to step 27, the mathematical derivative of the contrast curve, indicative of the inflection point, is determined. It is well known that the point of maximum slope on a curve can be determined by using a conventional 3-consecutive-point derivative algorithm in which three equally spaced consecutive data points along the curve are sampled and used to calculate the slope of the curve at the second (middle) data point. In accordance with the present invention, three points are still used to determine the derivative of the contrast curve, but the separation of the first and third sample derivative points (i.e., the width of the derivative base interval) is linked to real time in the image evolution via the image frame number. Specifically, the width of the derivative base interval at any selected point along the contrast curve is made proportional to the square-root of the IR image frame number, Z.

In this manner, the signal-to-noise (S/N) characteristics are maximized even in the midst of high noise levels. This improvement in the S/N ratio results from "sampling" over a larger interval and, thus, detects the largest signal change rather than the differential change traditionally obtained with fixed-width 3-point differentiation. Since a maximum S/N ratio is obtained when the sample point separation is equal to the full Gaussian width, the maximum possible S/N ratio is always achieved by using the frame-number proportional-width approach of the present invention.

Next, with reference to step 28, all peaks in the derivative curve are identified and a significance "weighting" factor is used to assess the proper peak to use as the $t_{infl}$ inflection point. During this step, a list of all peak locations (times) and amplitudes is maintained in computer memory. By applying a predetermined appropriate weighting function to the peak list, it is possible to adjust the significance of each peak so that, for example, peak-producing noise effects arising early in the data acquisition time are effectively discounted. Since empirical evidence indicates that peaks occurring later in time tend to be more significant, a temporal weighting function is implemented in the present example embodiment by simply multiplying the amplitude of a peak by the time at which it occurred. The peaks are then sorted according to decreasing significance (weight) and the peak having the greatest weighting value (i.e., the most significant) is selected as indicative of the proper inflection point.

Next, with reference to step 29, the thickness of the object at the location of the resolution element corresponding to the selected pixel is determined. This is accomplished by identifying the frame number in which the most significant peak occurs and converting that value to real time. Since IR image frame acquisition occurs at a predetermined known rate, a frame number can be equated to a real elapsed time. Accordingly, the frame number of the IR image frame harboring the most significant peak provides a time value for $t_{infl}$. Using Equs. (1) and (2) above, this value for $t_{infl}$ is converted to a thickness value, L, relating the actual thickness of the object at the location of the resolution element corresponding to the pixel.

Next, with reference to step 30, the thickness value, L, is stored in memory and used to create a color-mapped (or gray-scale) image of the region of interest on the object surface for display or print, each color corresponding to a particular thickness. The next pixel is then selected (at step 23) and the above steps are performed again for each pixel comprising the IR image.

In addition to the steps outlined above, the input and selection of various parameter values such as diffusivity constant, data analysis starting point and range, temporal smoothing window size range, and color mapping range are automated for accuracy and consistency through appropriate conventional programming of the system control computer.

By conducting the transient thermography analysis using the above described steps for thermal data acquisition and analysis in conjunction with the above described apparatus in accordance with the present invention, wall thickness values can be accurately obtained even between closely spaced back wall or internal structures that may form a part of, or be connected to, the tested object—e.g., the rib-like structures often found in turbine air foils (as pictured in FIG. 1)—whereas using traditional thermal or ultrasonic methods such closely positioned back-wall structures would normally result in blurred images and distorted data.

Another embodiment of the present invention does away with the need to obtain contrast values for each pixel. In this embodiment, the occurrences in time of the inflection point in the pixel T-t intensity curves corresponding to a resolution element both of the object being measured and a reference block having one or more portions of known thickness are determined and compared. The occurrence in time of the reference block inflection point(s) relative to the inflection point for the object indicates the object thickness. If the object inflection point falls between inflection points corresponding to two portions of different thickness on the block, interpolation can provide the object thickness. While in the preferred embodiment pixel contrast is determined as noted above using a thermally thick reference, useful measurements could be provided without determining pixel contrast by using only pixel intensity inflection points.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A high speed infrared (IR) transient thermography method for determining the thickness of an object, comprising the steps of:
   a) storing pixel intensity data from a predetermined sequence of image frames acquired from an IR sensitive focal-plane array camera, wherein each sequentially acquired image frame is assigned a frame number of increasing value that linearly corresponds to elapsed time;
   b) determining a pixel contrast curve from the pixel intensity data for a pixel from said sequence of image frames;
   c) performing Gaussian temporal smoothing of pixel contrast curve data developed in step (b);
   d) determining a time derivative of the pixel contrast curve data from separate data points in time along the contrast curve after Gaussian temporal smoothing;
   e) identifying localized peak derivative values in the time derivative of the pixel contrast curve data;
   f) applying a predetermined weighting function to said localized peak values identified in step (e) to determine a significance value for each derivative peak value identified;
   g) selecting one contrast curve derivative peak value based on a most significant value determined in step (f); and
   h) determining an object thickness, L, based on a frame number of an image frame in which the contrast curve derivative peak selected in step (g) occurs.

2. The IR transient thermography method of claim 1 wherein the pixel contrast curve is determined by subtracting pixel reference curve data from pixel intensity data for a pixel.

3. The IR transient thermography method of claim 2 wherein the pixel reference curve data is determined from pixel intensity data of a thermally thick reference portion of the object, said reference portion approximating the characteristics of a hypothetical infinitely thick object.

4. The IR transient thermography method of claim 2 wherein the pixel reference curve data is determined from pixel intensity data obtained from a thermally thick region of a separate metal reference article having substantially similar heat conduction characteristics imaged along with the object.

5. The IR transient thermography method of claim 1 wherein variable emissivity caused by surface curvatures and/or variable surface conditions of an imaged object are compensated by modifying pixel intensity data by a predetermined gain factor for selected pixels.

6. The IR transient thermography method of claim 1 wherein pixel intensity data for selected pixels is modified to compensate for the effects of varying IR emissivity due to surface curvatures of the object.

7. The IR transient thermography method of claim 1 wherein a pixel intensity curve comprising pixel intensity data acquired over a predetermined time period is offset by matching selected points in the pixel intensity curve with selected points in a normalized pixel reference curve.

8. The IR transient thermography method of claim 1 wherein a temporal smoothing window size employed for Gaussian smoothing of pixel contrast curve data is proportional to a frame number that corresponds to a beginning time of a smoothing window such that smoothing window size increases with time.

9. The IR transient thermography method of claim 1 wherein temporal smoothing window size employed for Gaussian smoothing of pixel contrast curve data is proportional to a square-root of a frame number that corresponds to a beginning time of a smoothing window.

10. The IR transient thermography method of claim 1 wherein a time derivative of the pixel contrast curve data is developed by using a conventional three-point derivative algorithm modified by selecting three data points along the contrast curve, equally separated in time, such that the first and third data points are separated by a time period proportional to a square-root of the frame number value for the second (middle) data point.

11. The IR transient thermography method of claim 1 wherein thickness, L, is determined according to the following equations:

$$T_c = 4L^2/\pi^2 \alpha$$

and $$t_{infl} = 0.9055 T_c$$

wherein $\alpha$ is the thermal diffusivity of the object, and where $t_{infl}$ is directly related to a value of a frame number of an image frame in which a contrast curve derivative peak of greatest significance occurs.

12. The IR transient thermography method of claim 1 wherein the object is coated with a thin layer of a high ultraviolet-visible infrared emissivity substance prior to acquiring IR image frames.

13. An apparatus for determining a thickness of an object having a surface which can be visualized as an array of pixels, comprising:
   a heat source for rapidly heating the surface of an object;
   a means for recording pixel intensity in a sequence of IR images;

a means for determining pixel contrast data from recorded pixel intensity;

a means for determining a derivative of the contrast data based on a frame number value assigned to an IR image; and a means for determining thickness of the object relative to other portions of the object based upon pixel contrast and image frame number.

14. A high speed infrared (IR) transient thermography method for determining the actual thickness of an object, comprising the steps of:

a) acquiring pixel intensity data from a predetermined sequence of IR image frames of the object using an IR sensitive focal-plane array camera, each image frame comprising a plurality of pixels;

b) obtaining a value representing an average pixel intensity from pixel intensity data corresponding to a thermally thick reference portion of the object;

c) determining pixel contrast data by subtracting said value representing average pixel intensity from pixel intensity data for a pixel;

d) repeating steps (b) and (c) for each frame of said sequence of IR image frames to develop a temperature-time (T-t) contrast curve for said pixel; and e) determining actual thickness at a resolution element of the object corresponding to the pixel using said contrast curve, said determination based on a heat-flow invariant relationship between an inflection point in the contrast curve and a heat-flow characteristic time dependent upon a thermal diffusivity of the object.

15. The IR transient thermography method of claim 14 wherein the step of determining actual thickness at a resolution element of the object corresponding to the pixel using said contrast curve further comprises the steps of:

performing temporal smoothing of pixel contrast curve data;

determining a time derivative of the pixel contrast curve data from separate data points in time along the contrast curve;

identifying localized peak derivative values in the time derivative of the pixel contrast curve data;

applying a predetermined weighting function to said localized peak values to determine a significance value for each derivative peak value identified;

selecting one contrast curve derivative peak value based on said significance value; and determining actual object thickness at said resolution element based on a frame number of an image frame in which a selected contrast curve derivative peak value occurs.

16. The IR transient thermography method of claim 15 wherein a smoothing function window size employed for temporal smoothing of pixel contrast curve data is proportional to a frame number that corresponds to a beginning time of a smoothing window such that smoothing window size increases with time.

17. The IR transient thermography method of claim 15 wherein a temporal smoothing window size employed for Gaussian smoothing of pixel contrast curve data is proportional to a square-root of a frame number that corresponds to a beginning time of a smoothing window.

18. A high speed infrared (IR) transient thermography method for determining the actual thickness of an object, comprising the steps of:

a) acquiring pixel intensity data from a predetermined sequence of IR image frames of the object and an adjacent separate reference article imaged along with the object using an IR sensitive focal-plane array camera, each image frame comprising a plurality of pixels and said reference article having a thermally thick reference portion of substantially similar heat conduction characteristics as the object;

b) obtaining a value representing an average pixel intensity from pixel intensity data corresponding to a thermally thick reference portion of the reference article;

c) determining pixel contrast data by subtracting said value representing average pixel intensity from pixel intensity data for a pixel;

d) repeating steps (b) and (c) for each frame of said sequence of IR image frames to develop a temperature-time (T-t) contrast curve for said pixel; and e) determining actual thickness at a resolution element of the object corresponding to the pixel using said contrast curve, said determination based on a heat-flow invariant relationship between an inflection point in the contrast curve and a heat-flow characteristic time dependent upon a thermal diffusivity of the object.

19. The high speed infrared (IR) transient thermography method of claim 18 wherein the step of determining actual thickness at a resolution element of the object corresponding to the pixel using said contrast curve further comprises the steps of:

performing temporal smoothing of pixel contrast curve data;

determining a time derivative of the pixel contrast curve data from separate data points in time along the contrast curve;

identifying localized peak derivative values in the time derivative of the pixel contrast curve data;

applying a predetermined weighting function to said localized peak values to determine a significance value for each derivative peak value identified;

selecting one contrast curve derivative peak value based on said significance value; and determining actual object thickness at said resolution element based on a frame number of an image frame in which a selected contrast curve derivative peak value occurs.

20. The IR transient thermography method of claim 19 wherein a smoothing function window size employed for temporal smoothing of pixel contrast curve data is proportional to a frame number that corresponds to a beginning time of a smoothing window such that smoothing window size increases with time.

21. The IR transient thermography method of claim 19 wherein a temporal smoothing window size employed for Gaussian smoothing of pixel contrast curve data is proportional to a square-root of a frame number that corresponds to a beginning time of a smoothing window.

22. A high speed infrared (IR) transient thermography method for determining the actual thickness of an object, comprising the steps of:

a) acquiring pixel intensity data from a predetermined sequence of IR image frames of the object and an adjacent separate reference article imaged along with the object using an IR sensitive focal-plane array camera, each image frame comprising a plurality of pixels, and said reference article having a one or more discrete portions of known thickness and substantially similar heat conduction characteristics as the object;

b) determining inflection points in pixel T-t intensity curves corresponding to a resolution element of the object and one or more resolution elements corresponding to different portions of known thickness on the reference article; and c) determining an actual thickness of the object at the resolution element of the object by comparing relative times of occurrence of the inflection points determined in step (b) and extrapolating or interpolating a thickness value for the object from the portions of known thickness on the reference article.

* * * * *